US007272435B2

(12) United States Patent
Rowlandson (10) Patent No.: US 7,272,435 B2
(45) Date of Patent: Sep. 18, 2007

(54) SYSTEM AND METHOD FOR SUDDEN CARDIAC DEATH PREDICTION (75) Inventor: G. Ian Rowlandson, Milwaukee, WI (US)

(73) Assignee: GE Medical Information Technologies, Inc., Waukesha, WI (US)

(*) Notice: Subject to any disclaimer, the term of this patent is extended or adjusted under 35 U.S.C. 154(b) by 131 days.

(21) Appl. No.: 10/825,534

(22) Filed: Apr. 15, 2004

(65) Prior Publication Data
US 2005/0234355 A1 Oct. 20, 2005

(51) Int. Cl.
A61B 5/04 (2006.01)

(52) U.S. Cl. ............... 600/513; 600/515; 128/922

(58) Field of Classification Search ......... 128/920, 128/922; 600/513, 515
See application file for complete search history.

(56) References Cited

U.S. PATENT DOCUMENTS

| 3,554,187 A * | 1/1971 | Glassner et al. ............ 600/516 |
|---|---|---|
| 3,658,055 A * | 4/1972 | Abe et al. ................... 600/516 |
| 3,759,248 A | 9/1973 | Valiquette |
| 3,821,948 A | 7/1974 | King |
| 3,902,479 A | 9/1975 | Chaumet |
| 3,952,731 A | 4/1976 | Worstencroft |
| 4,124,894 A | 11/1978 | Vick et al. |
| 4,136,690 A | 1/1979 | Anderson et al. |
| 4,170,992 A | 10/1979 | Dillman |
| 4,181,135 A | 1/1980 | Andresen et al. |
| 4,202,340 A | 5/1980 | Langer et al. |
| 4,316,249 A | 2/1982 | Gallant et al. |
| 4,417,306 A | 11/1983 | Citron et al. |
| 4,422,459 A | 12/1983 | Simson |
| 4,432,375 A | 2/1984 | Angel et al. |
| 4,457,315 A | 7/1984 | Bennish |
| 4,458,691 A | 7/1984 | Netravali |
| 4,458,692 A | 7/1984 | Simson |
| 4,475,558 A | 10/1984 | Brock |
| 4,492,235 A | 1/1985 | Sitrick |
| 4,519,395 A | 5/1985 | Hrushesky |
| 4,583,553 A | 4/1986 | Shah et al. |
| 4,589,420 A | 5/1986 | Adams et al. |
| 4,603,703 A | 8/1986 | McGill et al. |
| 4,616,659 A | 10/1986 | Prezas et al. |
| 4,665,485 A | 5/1987 | Lundy et al. |

(Continued)

FOREIGN PATENT DOCUMENTS

DE 2604460 8/1977

(Continued)

OTHER PUBLICATIONS

Verrier et al., 'Behavioral states and sudden cardiac death,' Pace, Sep. 1992, 15, pp. 1387-1393.

(Continued)

Primary Examiner—Carl Layno
Assistant Examiner—Tammie K. Heller
(74) Attorney, Agent, or Firm—Andrus, Sceales, Starke & Sawall, LLP (57) ABSTRACT A device that calculates a sudden cardiac death score based on acquired patient data. A system and method that combines independent indications of sudden cardiac death to predict sudden cardiac death. The system can include various cardiology test systems interconnected to a sudden cardiac death prediction system.

9 Claims, 5 Drawing Sheets

U.S. PATENT DOCUMENTS

| | | | |
|---|---|---|---|
| 4,679,144 A | | 7/1987 | Cox et al. |
| 4,680,708 A | * | 7/1987 | Ambos et al. ............... 600/509 |
| 4,732,157 A | | 3/1988 | Kaplan et al. |
| 4,796,638 A | | 1/1989 | Sasaki |
| 4,802,491 A | | 2/1989 | Cohen et al. |
| 4,832,038 A | | 5/1989 | Arai et al. |
| 4,854,327 A | | 8/1989 | Kunig |
| 4,860,762 A | | 8/1989 | Heumann et al. |
| 4,896,677 A | | 1/1990 | Kaneko et al. |
| 4,924,875 A | | 5/1990 | Chamoun |
| 4,928,690 A | | 5/1990 | Heilman et al. |
| 4,938,228 A | | 7/1990 | Righter et al. |
| 4,951,680 A | | 8/1990 | Kirk et al. |
| 4,955,382 A | | 9/1990 | Franz et al. |
| 4,957,115 A | * | 9/1990 | Selker ......................... 600/509 |
| 4,958,641 A | | 9/1990 | Digby et al. |
| 4,972,834 A | | 11/1990 | Begemann et al. |
| 4,974,162 A | | 11/1990 | Siegel et al. |
| 4,974,598 A | | 12/1990 | John |
| 4,977,899 A | | 12/1990 | Digby et al. |
| 4,979,510 A | | 12/1990 | Franz et al. |
| 4,989,610 A | | 2/1991 | Patton et al. |
| 4,998,535 A | | 3/1991 | Selker et al. |
| 5,000,189 A | | 3/1991 | Throne et al. |
| 5,010,888 A | | 4/1991 | Jadvar et al. |
| 5,020,540 A | | 6/1991 | Chamoun |
| 5,025,795 A | | 6/1991 | Kunig |
| 5,042,497 A | * | 8/1991 | Shapland ..................... 600/509 |
| 5,092,341 A | | 3/1992 | Kelen |
| 5,109,862 A | | 5/1992 | Kelen et al. |
| 5,117,833 A | | 6/1992 | Albert et al. |
| 5,117,834 A | | 6/1992 | Kroll et al. |
| 5,148,812 A | | 9/1992 | Verrier et al. |
| 5,188,116 A | | 2/1993 | Pommrehn et al. |
| 5,201,321 A | | 4/1993 | Fulton |
| 5,234,404 A | | 8/1993 | Tuttle et al. |
| 5,253,650 A | | 10/1993 | Wada |
| 5,265,617 A | | 11/1993 | Verrier et al. |
| 5,276,612 A | * | 1/1994 | Selker ......................... 600/523 |
| 5,277,188 A | * | 1/1994 | Selker ......................... 600/508 |
| 5,277,190 A | | 1/1994 | Moulton |
| 5,323,783 A | | 6/1994 | Henkin et al. |
| 5,343,870 A | | 9/1994 | Gallant et al. |
| 5,423,878 A | | 6/1995 | Franz |
| 5,437,285 A | * | 8/1995 | Verrier et al. ............... 600/515 |
| 5,501,229 A | | 3/1996 | Selker et al. |
| 5,509,425 A | * | 4/1996 | Feng ........................... 600/515 |
| 5,533,522 A | * | 7/1996 | Feng ........................... 600/544 |
| 5,542,429 A | * | 8/1996 | Feng ........................... 600/515 |
| 5,560,370 A | | 10/1996 | Verrier et al. |
| 5,570,696 A | | 11/1996 | Arnold et al. |
| 5,649,544 A | * | 7/1997 | Feng ........................... 600/509 |
| 5,718,233 A | | 2/1998 | Selker et al. |
| 5,724,983 A | * | 3/1998 | Selker et al. ............... 600/301 |
| 5,747,274 A | | 5/1998 | Jackowski |
| 5,819,007 A | * | 10/1998 | Elghazzawi .................. 706/46 |
| 5,819,741 A | | 10/1998 | Karlsson et al. |
| 5,921,940 A | | 7/1999 | Verrier et al. |
| 5,935,082 A | | 8/1999 | Albrecht et al. |
| 6,059,724 A | | 5/2000 | Campell et al. |
| 6,067,466 A | * | 5/2000 | Selker et al. ............... 600/513 |
| 6,099,469 A | | 8/2000 | Armstrong et al. |
| 6,142,078 A | | 11/2000 | Lachajewski |
| 6,169,919 B1 | | 1/2001 | Nearing et al. |
| 6,226,549 B1 | * | 5/2001 | Deco et al. .................. 600/518 |
| 6,261,230 B1 | * | 7/2001 | Bardy ......................... 600/300 |
| 6,277,072 B1 | * | 8/2001 | Bardy ......................... 600/300 |
| 6,334,192 B1 | | 12/2001 | Karpf |
| 6,370,423 B1 | * | 4/2002 | Guerrero et al. ............ 600/513 |
| 6,394,952 B1 | | 5/2002 | Anderson et al. |
| 6,443,889 B1 | | 9/2002 | Groth et al. |
| 6,450,954 B1 | | 9/2002 | Selker |
| 6,453,191 B2 | | 9/2002 | Krishnamachari |
| 6,507,753 B1 | | 1/2003 | Xue et al. |
| 6,516,219 B1 | * | 2/2003 | Street ......................... 600/515 |
| 6,705,991 B2 | * | 3/2004 | Bardy ......................... 600/300 |
| 2002/0188214 A1 | * | 12/2002 | Misczynski et al. ........ 600/516 |
| 2003/0191403 A1 | * | 10/2003 | Zhou et al. .................. 600/515 |
| 2004/0230456 A1 | * | 11/2004 | Lozier et al. .................. 705/2 |
| 2005/0004481 A1 | * | 1/2005 | Xue et al. .................... 600/509 |

FOREIGN PATENT DOCUMENTS

| | | |
|---|---|---|
| DE | 3303104 | 8/1984 |
| DE | 4024360 | 3/1991 |
| EP | 0080821 | 6/1983 |
| FR | 2539978 | 8/1984 |
| GB | 2070871 | 9/1981 |
| WO | WO81/02832 | 10/1981 |

OTHER PUBLICATIONS

Turito et al., 'Alternans of the ST segments in variant angina,' Chest, Mar. 1988, 93(3), pp. 587-591.

Ring et al., 'Exercise-induced ST segment alternans,' American Heart Journal, May 1986, 111(5), pp. 1009-1011.

Wayne et al., 'Exercise-induceed ST segment alternans,' Chest, May 1983, 83(5), pp. 824-825.

Verrier et al., 'Ambulatory electrocardiogram-based tracking of T wave alternans in postmyocardial infarction patients to assess risk of cardiac arrest or arrhythmic death,' Journal of Cardiovascular Electrophysiology, Jul. 2003, 14(7), pp. 705-711.

Little et al., 'Torsade de Pointes and T-U wave alternans associated with arsenic poisoning,' Pace, 1990, 13, pp. 164-170.

Weintraub et al., 'The congenital long QT syndromes in childhood,' Journal of the American College of Cardiology, Sep. 1990, 16(3), pp. 674-680.

Bibler et al., 'Recurrent ventricular tachycardia due to pentamidine-induced cardiotoxicity,' Chest, Dec. 1988, 94(6), pp. 1303-1306.

Ahnve et al., 'Circadian variations in cardiovascular parameters during sleep deprivation, A noninvasive study of young healthy men,' European Journal of Applied Physiology, 1981, 46, pp. 9-19.

Surawicz, 'ST-segment, T-wave, and U-wave changes during myocardial ischmeia and after myocardial infarction,' Canadian Journal of Cardiology, Supplement A, Jul. 1986, pp. 71A-84A.

Mitsutake et al., 'Usefulness of the Valsalva Maneuver in management of the long QT syndrome,' Circulation, 1981, 63(5), pp. 1029-1035.

Nearing et al., 'Personal computer system for the tracking cardiac vulnerability by complex demodulation of the T wave,' American Physiological Society, 1993, pp. 2606-2612.

Joyal et al., 'ST-segment alternans during percutaneous transluminal coronary angioplasty,' Division of Cardiology, Department of Medicine, University of Florida and the Veterans Administration Medical Center, Jun. 1984, pp. 915-916.

Schwartz et al., 'Electrical alternation of the T-wave: clinical and experimental evidence of its relationship with the sympathetic nervous system and with the long Q-T syndrome,' American Heart Journal, Jan. 1975, 89(1), pp. 45-50.

Schwartz, 'Idiopathic long QT syndrome: progress and questions,' American Heart Journal, Feb. 1985, 109(2), pp. 399-411.

Verrier et al., 'Electrophysiologic basis for T wave alternans as an index of vulnerability to ventricular fibrillation,' Journal of Cardiovascular Electrophysiology, May 1994, 5(5), pp. 445-461.

Speranza et al., 'Beat-to-beat measurement and analysis of the R-T interval in 24 h ECG Holter recordings,' Med and Biol Eng & Comput, 1993, 31, pp. 487-494.

Narayanaswamy et al., 'Selective beat signal averaging and spectral analysis of beat intervals to determine the mechanisms of premature ventricular contractions,' University of Oklahoma Health Sciences Center, May 1993, pp. 81-84.

Laks et al., 'ECG computer program developed for a retrospective and prospective study of the Pardee T wave,' Department of Medicine, UCLA School of Medicine, Harbor-UCLA Medical Center, Torrence, CA, 1992, pp. 365-368.

Makarov et al., Holter monitoring in the long QT syndrome of children and adolscents, Cor Vasa, 1990, 32(6), pp. 474-483.

Navarro-Lopez et al., "Isolated T wave alternans elicited by hypocalcernia in dogs," Electrocardiology, 1978, 11(2), pp. 103-108.

Stroobandt et al., "Simultaneous recording of atrial and ventricular monphasic action potential duration during atrial pacing, ventricular pacing and ventricular fibrillation," Pace, Jul.-Aug. 1985, 8, pp. 502-511.

Sharma et al., "Romano-Ward prolonged OT syndrome with intermittent T wave alternans and atrioventricular block," American Heart Journal, 1981, pp. 500-501.

Navarro-Lopez et al., "Isolated T wave alternans," American Heart Journal, 1978, pp. 369-374.

Ryan, et al.; ACC/AHA Guidelines for the Management of Patients With Acute Myocardial Infarction; Journal of the American College of Cardiology; vol. 28, No. 5, Nov. 1, 1996; 1328-428.

Ryan, et al.; 1999 Update: ACC/AHA Guidelines for the Management of Patients With Acute Myocardial Infarction; Journal of the American College of Cardiology; vol. 34, No. 3, Sep. 1999; 890-911.

Circulation; American Heart Association; ECC Guidelines, Part 7: The Era of Reperfusion http://circ.ahajournals.org/cgi/content/full/102/suppl_/I-172?maxtoshow+HIRA=10&hits=10&RES;2000; 102: I-172.

Kudenchuk, et al., Accuracy of Computer-Interpreted Electrocardiography in Selecting Patients for Thrombolytic Therapy; Journal of the American College of Cardiology; vol. 17, No. 7, Jun. 1991, 1486-91.

O'Rourke, et al.; Accuracy of a Portable Interpretive ECG Machine in Diagnosis of Acute Evolving Myocardial Infarction; Aust NZ J Med 1992; 22; 9-13.

Dr. Richard Saumarez, Multi disciplinary approach to sudden cardiac death, University of Cambridge Department of Engineering, http://www-g.eng.cam.ac.uk/mmg/biomedical/saumarez.html, 2000.

Prevention of Sudden Death From Ventricular Arrhythmia, http://www.ccs.ca, 1999.

Braunwald, et al.; ACC/AHA Guidelines for the Management of Patients With Unstable Angina and Non-ST-Segment Elevation Myocardial Infarction, Journal of the American College of Cardiology; vol. 36, No. 3, Sep. 2000; 970-1062.

* cited by examiner

SYSTEM AND METHOD FOR SUDDEN CARDIAC DEATH PREDICTION

BACKGROUND OF THE INVENTION

Sudden cardiac death ("SCD") can be generally defined as death within one hour of the onset of symptoms without a previously-known disease or a disease that was expected to be lethal. SCD can also occur without symptoms or warnings signs. SCD is often described with respect to an unwitnessed death with the victim having been known to be alive less than 24 hours earlier.

SCD can kill its victims within minutes and often occurs in outwardly healthy people who have no known heart disease. Although it may occur in outwardly healthy people, most victims do have heart disease or other health problems, often without being aware of it. SCD claims about 300,000 lives a year in the United States and presents a public health challenge in that often the only indication a patient is at risk appears when the patient succumbs, without warning, to a heart failure episode.

In many cases, SCD victims suffer from ventricular tachycardia that degenerates into ventricular fibrillation. Ventricular tachycardia is a type of cardiac arrhythmia that is a serious, often-times, fatal condition characterized by rapid, uncontrolled, and ineffective beating of the heart. Ventricular fibrillation is a chaotic ventricular heart rhythm which produces little or no net blood flow from the heart, such that there is little or no net blood flow to the brain and other organs. Ventricular fibrillation, if not terminated, results in death. Researchers continue their efforts to predict the onset and triggers for such ventricular tachyarrhythmias and SCD.

BRIEF DESCRIPTION OF THE INVENTION

As the underlying physiological causes of cardiac arrhythmias are not fully understood, SCD and its corresponding arrhythmias are difficult to accurately predict. Accordingly, one embodiment of the invention includes a method of more accurately predicting sudden cardiac death in a patient. The method comprises acquiring patient data from a plurality of medical equipment databases and analyzing the patient data to determine a sudden cardiac death risk score.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
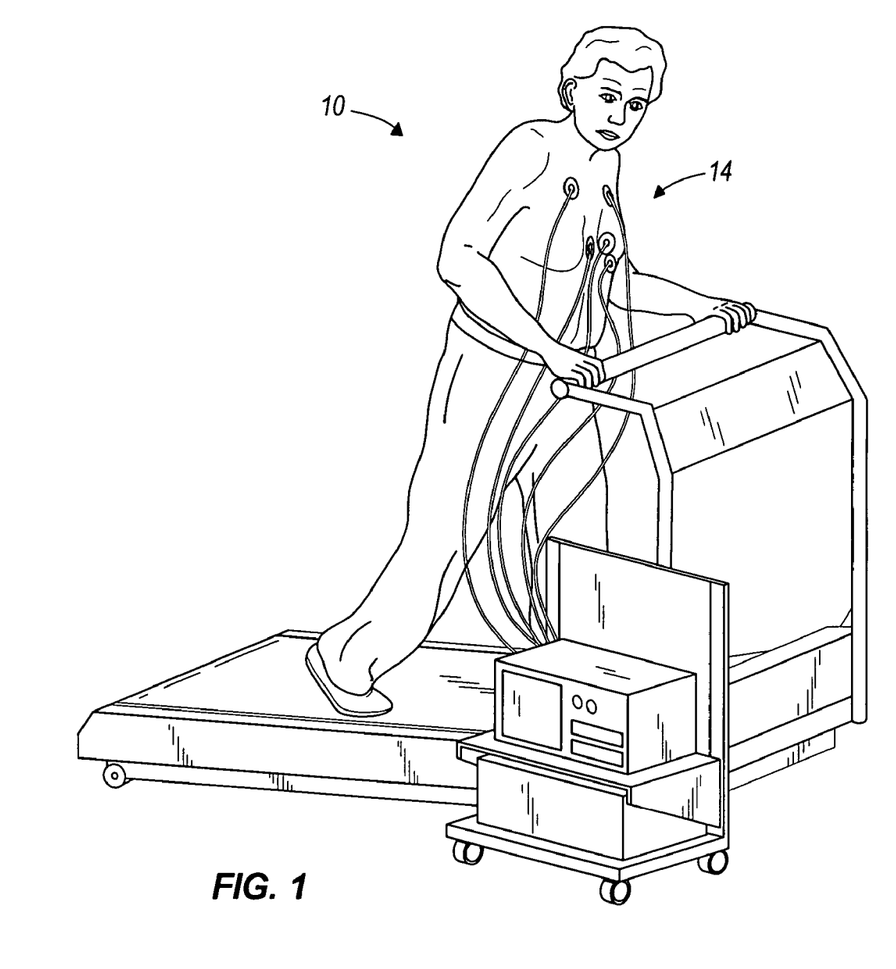
FIG. 1 illustrates a patient undergoing a medical test procedure.

FIG. 1 illustrates a patient 10 that is undergoing a medical test procedure in a medical care facility. The patient 10 may have arrived at the medical care facility for a variety of reasons, such as, for example, to receive an annual physical, for a scheduled surgery, for a medical test procedure prescribed by the patient's doctor, for an emergency, or for other reasons. Generally, if the patient 10 is experiencing chest pain or other heart-related symptoms, medical personnel prescribes various tests to diagnose the patient's problem(s). For example, the patient 10 can undergo an electrocardiogram ("ECG") test, a stress test, a stress-echo test, a stress-nuclear test, a cardiac catheterization (also known as an angiogram), an electrophysiology study, and/or other medical test procedures.

FIG. 1 also illustrates the patient 10 with electrodes 14 connected to his or her chest. The electrodes 14 can be connected to a medical device that acquires and/or records the patient's ECG. Two or more electrodes 14 can be positioned on the patient's chest to acquire an ECG. In the embodiment shown in FIG. 1, the patient 10 is undergoing a stress test on a treadmill. However, FIG. 1 only illustrates one of the many tests that the patient 10 can undergo. The various medical tests are well-known in the art and will not be specifically illustrated in the drawings.

Some of the various medical tests known in the art that are relevant to SCD are briefly described in the following several paragraphs. An ECG test is a noninvasive test that records the electrical activity of the heart. The electrical activity is related to the impulses that travel through the heart that determine the heart's rate and rhythm. An ECG test evaluates the patient's cardiac condition and determines if a heart attack has occurred; what part of the heart is damaged; if there are any irregular heart beats or rhythms; and if there is a decreased supply of blood and oxygen to the heart.

A stress test is a non-invasive procedure that combines a treadmill stress test and an ECG. Electrodes 14 are placed on the patient's chest to monitor the heart's rate and rhythm throughout the test and to obtain and monitor the patient's ECG at rest, during exercise, and during recovery. The medical personnel identifies changes in the ECG pattern and any symptoms that the patient may experience. Specifically, the medical personnel can evaluate the patient's cardiac condition related to irregular heart rhythms; whether there is a decreased supply of blood and oxygen to the heart at rest as well as with exercise; overall level of cardiovascular conditioning; how hard the heart can work before symptoms develop; how quickly the heart recovers after exercise; and what the exercise target heart rate should be.

A stress-echo test is a non-invasive procedure that combines a treadmill stress test and an echocardiogram ("ECHO"). Electrodes 14 are placed on the patient's chest to monitor the heart's rate and rhythm throughout the test and to obtain an ECG. An ECHO is done at rest prior to exercise and again at peak heart rate. The ECHO uses sound waves (e.g., ultrasound) to provide an image of the heart's internal structures, size, and movement. The patient exercises on the treadmill for a certain period of time. At the peak of exercise, the treadmill is stopped, and a second ECHO is obtained to visualize the heart's motion with exercise. The medical personnel looks for changes in the ECG pattern and any symptoms that the patient may experience. Specifically, the medical personnel can evaluate the patient's cardiac condition related to irregular heart rhythms; whether there is a decreased supply of blood and oxygen to the heart at rest, as well as with exercise; overall level of cardiovascular conditioning; how hard the heart can work before symptoms develop; and how quickly the heart recovers after exercise.

A stress-nuclear test is a procedure that combines a treadmill stress test and imaging using an isotope (e.g., CARDIOLITE®, manufactured by Dupont Merck Pharmaceutical Company or Thallium) to evaluate coronary blood flow. Electrodes 14 are placed on the patient's chest to monitor the heart' rate and rhythm throughout the test and to obtain an ECG. The patient exercises on the treadmill for a certain period of time. A small dose of the isotope is injected into the patient 10 at the peak of exercise. After exercise, a nuclear camera obtains images of the patient's heart. Additional images can be obtained of the patient's heart while at rest. During exercise, the medical personnel looks for changes in the ECG pattern and any symptoms that the patient may experience. Specifically, the medical personnel can evaluate the images to determine the specific area(s) of the heart that is not getting enough blood and oxygen; which area(s) of the heart has recovered, but is still not getting enough blood and oxygen; how quickly the heart recovers after exercise; any irregular heart rhythms; and whether the patient has had a heart attack in the past.

A cardiac catheterization procedure is non-surgical and is performed under X-ray guidance in the Cardiac Catheterization Lab. A catheter (a long, thin, flexible tube) is inserted through an artery in the thigh up into the heart. A colorless dye is injected through the catheter, and X-ray images are taken of the heart and coronary arteries. The medical personnel can evaluate the patient's cardiac condition related to how well the heart muscle and valves are working; the extent of damage to the heart after a heart attack; which coronary arteries are narrowed; the extent and degree of the narrowing; and what treatment is required (e.g., medical management, an angioplasty, or surgery).

An electrophysiology study is a test that evaluates the electrical system of the heart. This test is used to study irregular or abnormal heart rhythms that may be life-threatening so that proper treatment can be given to correct the problem and to determine which treatment will correct the problem. This procedure is non-surgical and performed under X-ray in a cardiac catheterization lab. One or more catheters (i.e., long, thin, flexible tubes) are inserted through the femoral vein in the groin. X-ray is used to guide the catheters up into the heart. The medical personnel stimulates the heart with small electrical signals to make it beat at various rates. If irregular rhythms occur, different medications can be given to determine which best corrects the irregularity and converts the heart back to a normal rhythm.

These tests can be performed in various settings, such as a hospital (in a cardiac catheterization lab, electrophysiology lab, emergency room, etc.), clinic, or doctor's office. The patient 10 can also be remotely monitored while at home for a longer period of time with various remote monitoring techniques, such as with a Holter monitor. If the patient 10 has an electronic implant (e.g., implantable cardioverter defibrillator, implanted cardiac defibrillator, automated implanted cardioverter defibrillator, pacemaker, etc.), the patient 10 can be monitored by downloading data from the electronic implant to a database for review by medical personnel.

Many of the tests described above are performed using equipment that is stand-alone and does not communicate or network with other equipment or systems. In addition, all of these tests produce various patient data, such as, images, results, and reports. Some of these tests can provide one or more measurements, such as, for example, ejection fraction, wall motion abnormalities, heart rate variability, heart rate turbulence, QRS duration, signal-averaged ECG, rhythm abnormalities, T-wave alternans, ST/T measurements, etc. Each of these measurements is described briefly in the following several paragraphs.

Heart rate variability ("HRV") is generally defined as the beat-to-beat variance in sinus cycle length over a period of time. A patient exhibiting low HRV shows a significantly increased risk of sudden cardiac death.

Ejection fraction ("EF") is the proportion, or fraction, of blood pumped out of the heart with each beat. A normal heart pumps out a little more than half the heart's volume of blood with each beat. A normal EF is 55 percent or higher.

A wall motion abnormality is an inadequate inward movement of the left ventricular wall during systole.

Heart rate turbulence is generally defined as the physiological, bi-phasic response of the sinus node to premature ventricular contractions. Heart rate turbulence consists of a short initial acceleration followed by a deceleration of the heart rate. Heart rate turbulence can be quantified by two numerical parameters, the turbulence onset and the turbulence slope. The premature ventricular contraction causes a brief disturbance of the arterial blood pressure (low amplitude of the premature beat, high amplitude of the ensuing normal beat). When the autonomic control system is intact, this fleeting change is registered immediately with an instantaneous response in the form of heart rate turbulence. If the autonomic control system is impaired, this reaction is either weakened or entirely missing.

QRS duration is generally a time series and/or waveform morphology measurement. ST/T measurements monitor the elevation or depression of the S-T segment of the ECG to determine the amount of oxygenated blood being pumped to the heart.

Signal averaged ECG ("SAECG") is a technique involving computerized analysis of small segments of a standard ECG in order to detect abnormalities, termed ventricular late potentials ("VLP"), that would be otherwise obscured by "background" skeletal muscle activity. VLPs reflect aberrant, asynchronous electrical impulses arising from viable isolated cardiac muscle bordering an infarcted area and are thought to be responsible for ventricular tachyarrhythmias.

T-wave alternans are generally defined as a "beat-to-beat" alternation in the T-wave portion of a patient's ECG. When visible on the ECG, these alternations have been associated with an increased likelihood of ventricular arrhythmia.

One or more of the measurements described above can be used to predict SCD, and each one of the tests described above can provide some type of independent indication of SCD. Each device described above can include a software program (described below) that uses one or more of the measurements described above to calculate a SCD score. The SCD score, resulting diagnosis, and other data can be presented on the display of the device and/or printed in a report.

In some situations, it can be beneficial to acquire all of the test data for the patient 10 from each device and combine the data to generate a SCD score. Conventionally, the medical personnel must manually review the images, results, and reports of the particular test(s) that the patient 10 has undergone to provide a diagnosis and a treatment plan for the patient.

Figure 2:
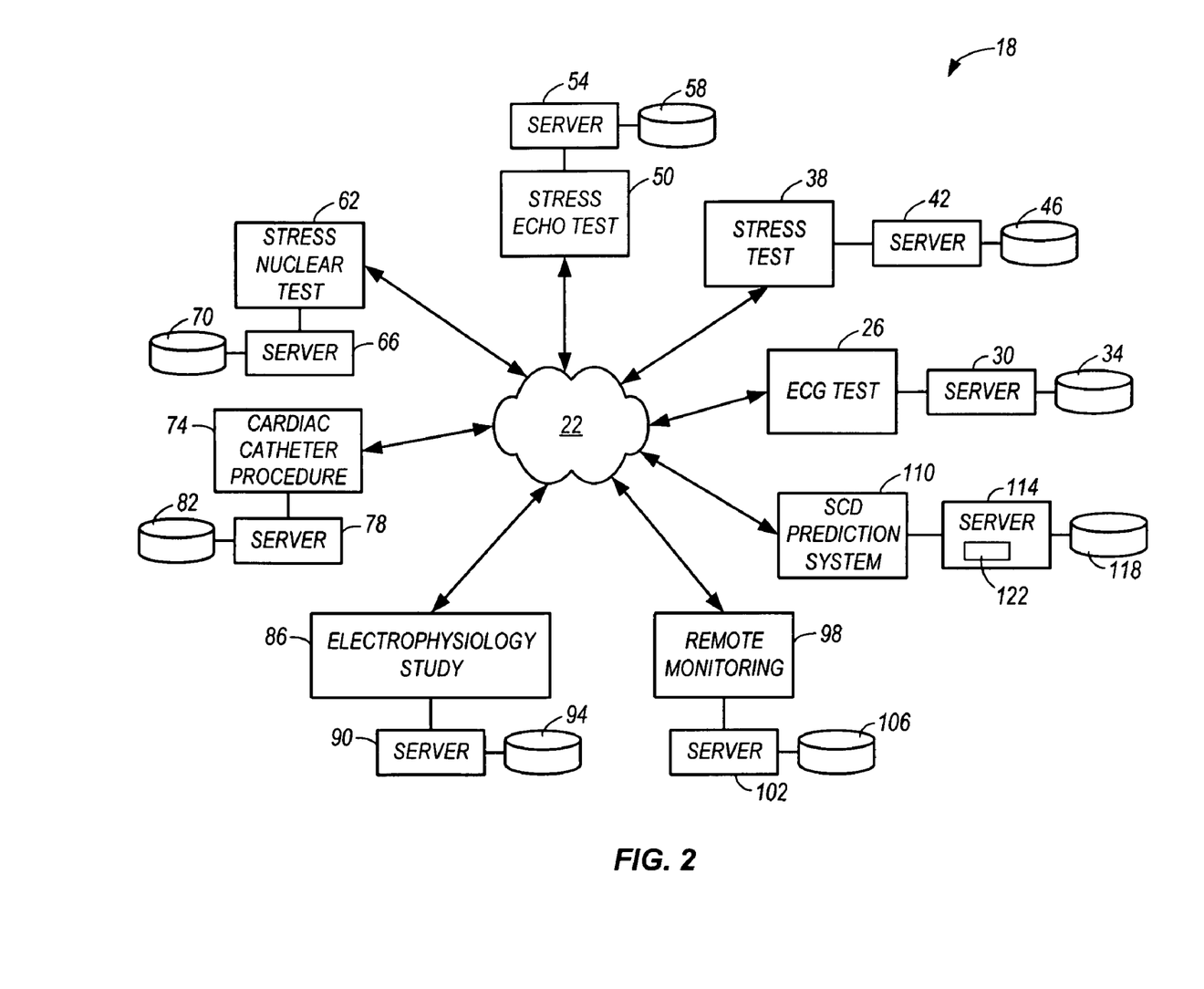
FIG. 2 is a schematic illustration of a sudden cardiac death prediction system according to one embodiment of the invention.

FIG. 2 illustrates a system 18 according to one embodiment of the invention that can interconnect the various pieces of medical equipment that can monitor the patient's heart and can perform the medical tests described above in order to generate patient data, such as, images, results, and reports. The system 18 can analyze the results from the various pieces of medical equipment and the results of the medical tests performed in order to generate a single medical report for use in predicting SCD.

Other embodiments of the invention can include fewer or more pieces of medical equipment or components than those shown in FIG. 2. The system 18 can include any suitable number and combination of pieces of medical equipment, modules, and/or components that can communicate over a network 22.

As shown in FIG. 2, the system 18 can include an ECG test system 26. The ECG test system 26 can include a server 30 and/or a database 34 for storing information related to ECGs. The server 30 can include an operating system for running various software programs and/or a communications application. The software programs can be manipulated by computer terminals (not shown) and/or medical equipment to acquire, enter, review, and/or save information.

The system 18 can also include a stress test system 38. The stress test system 38 can include a server 42 and/or a database 46 for storing information related to stress ECGs. The server 42 can include an operating system for running various software programs and/or a communications application. The software programs can be manipulated by computer terminals (not shown) and/or medical equipment to acquire, enter, review, and/or save information.

In addition, the system 18 can include a stress-echo test system 50. The stress-echo test system 50 can include a server 54 and/or a database 58 for storing information related to stress ECGs and echocardiograph images. The server 54 can include an operating system for running various software programs and/or a communications application. The software programs can be manipulated by computer terminals (not shown) and/or medical equipment to acquire, enter, review, and/or save information.

The system 18 can further include a stress-nuclear test system 62. The stress-nuclear test system 62 can include a server 66 and/or a database 70 for storing information related to stress ECGs and nuclear images. The server 66 can include an operating system for running various software programs and/or a communications application. The software programs can be manipulated by computer terminals (not shown) and/or medical equipment to acquire, enter, review, and/or save information.

The system 18 can still further include a cardiac catheterization system 74. The cardiac catheterization system 74 can include a server 78 and/or a database 82 for storing information related to ECGs and cardiac images. The server 78 can include an operating system for running various software programs and/or a communications application. The software programs can be manipulated by computer terminals (not shown) and/or medical equipment to acquire, enter, review, and/or save information.

The system 18 can also include an electrophysiology study system 86. The electrophysiology study system 86 can include a server 90 and/or a database 94 for storing information related to ECGs and cardiac images. The server 90 can include an operating system for running various software programs and/or a communications application. The software programs can be manipulated by computer terminals (not shown) and/or medical equipment to acquire, enter, review, and/or save information.

The system 18 can further include a remote monitoring system 98. The remote monitoring system 98 can include a Holter monitor or a telemetry transmitter that can save data and/or transmit data to the network 22 for storage in one or more of the databases.

The system 18 can still further include a SCD prediction system 110, which can interface and communicate with the ECG test system 26, the stress test system 38, the stress-echo test system 50, the stress-nuclear test system 62, the cardiac catheterization system 74, the electrophysiology system 86, and the remote monitoring system 98. The SCD prediction system 110 can include a server 114 and/or a database 118 for storing information related to patient data, ECGs, stress ECGs, echocardiograph images, nuclear images, X-ray images, ECG patterns, image patterns, decision support, mathematical equations, measurements, reports, diagnoses, tables, etc. The server 114 can include an operating system for running various software programs and/or a communications application. In particular, the server 114 can include a software program(s) 122 that operates to communicate with the ECG test system 26, the stress test system 38, the stress-echo test system 50, the stress-nuclear test system 62, the cardiac catheterization system 74, the electrophysiology system 86, and the remote monitoring system 98 through the network 22. The software program(s) 122 can be manipulated by a computer terminal(s) (not shown) and/or medical equipment to acquire, enter, review, analyze, and/or save information.

The network 22 can be built according to any networking technology or topology or combinations of technologies and topologies and can include multiple sub-networks. Connections between the systems shown in FIG. 2 can be made through local area networks ("LANs"), wide area networks ("WANs"), public switched telephone networks ("PSTNs"), Intranets, the Internet, or any other suitable networks. In a hospital or medical care facility, communication between the systems shown in FIG. 2 can be made through the Health Level Seven ("HL7") protocol with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

The two-way arrows in FIG. 2 generally represent two-way communication and information transfer between the network 22 and any one of the systems shown in FIG. 2. However, for some medical equipment, only one-way communication and information transfer may be necessary.

The SCD prediction system 110 can include a computer terminal (not shown) or any other suitable input/output device adapted to be accessed by medical personnel to determine and/or predict whether a patient may be at risk for sudden cardiac death. The computer terminal can include typical hardware such as a processor, I/O interfaces, and storage devices or memory. The computer terminal can also include input devices such as a keyboard and a mouse. The computer terminal can further include standard output devices, such as a monitor. In addition, the computer terminal can include peripherals, such as a printer and a scanner. The computer terminal can include software such as an operating system and a display application.

The SCD prediction system 110 can acquire all of the data available for the patient 10 from the systems shown in FIG. 2 in order to evaluate individual or combinations of test results and/or medical data (e.g., ejection fraction, wall motion abnormalities, heart rate variability, heart rate turbulence, QRS duration, signal averaged ECG, rhythm abnormalities, T-wave alternans, ST/T measurements, etc.) in order to generate a single medical report. The single medical report can include individual or combinations of test results and/or medical data and/or a diagnosis regarding the patient's risk for sudden cardiac death.

In many cases, the patient 10 has had a previous heart attack or myocardial infarction (i.e., a heart attack caused by blockage of a portion of the coronary artery which supplies blood to the heart muscle). As a result of the blockage, a portion of the heart muscle does not receive blood and therefore becomes scarred and diseased. The SCD prediction system 110 can acquire any data that is available for the patient 10 from tests performed in the past. For example, the patient 10 may have experienced a prior heart attack or another medical problem (cardiology related or non-cardiology related) that led to the conduction of a one or more of the above-described medical test procedures. If the test data was not electronically stored, but is in paper form, the test data can be scanned into or otherwise captured by the SCD prediction system 110. The SCD prediction system 110 can then analyze differences or changes in the patient's heart condition and provide the single medical report including a prediction of sudden cardiac death.

Figure 3:
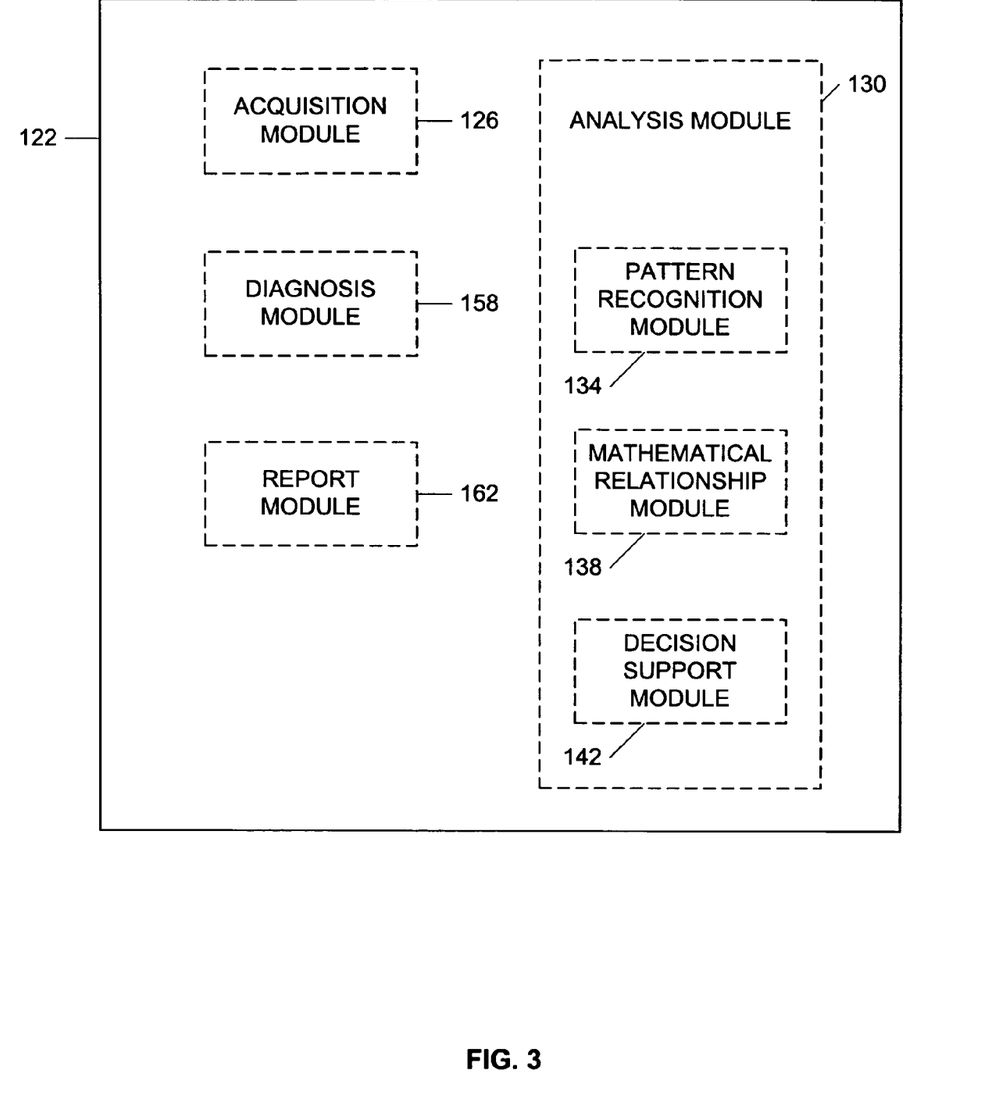
FIG. 3 is a block diagram of a software program that can be used in the sudden cardiac death prediction system of FIG. 2.

Referring to FIG. 3, the software program(s) 122 of the SCD prediction system 110 can include an acquisition module 126, which can acquire the data linked to the patient 10 that is stored in any of the databases 34, 46, 58, 70, 82, 94, and 118. The data can include measurements; raw data; unanalyzed data; analyzed data; medical personnel conclusions; images; charts; graphs; identified abnormalities; normal and abnormal ranges; patient identifiers (e.g., name, age, sex, weight, race); patient history (e.g., cholesterol level, diabetes, family history, smoking, blood pressure, obesity); symptoms; dates of reports and tests; and identification of prescribing, attending and reading physicians, etc.

The software program(s) 122 can also include an analysis module 130, which can analyze the acquired data for the patient 10. The analysis module 130 can include a pattern recognition module 134, a mathematical relationship module 138, a decision support module 142, and any additional modules suitable for analyzing the acquired data.

The pattern recognition module 134 can store ECG patterns for ECGs having known or assigned conditions and diagnoses. The pattern recognition module 134 can also store image patterns for images having known or assigned conditions and diagnoses. The pattern recognition module 134 can provide ECG measurements based on the similarities and differences between the patient's ECGs and the stored ECG patterns. The pattern recognition module 134 can also provide image measurements based on the similarities and differences between the patient's images and the stored image patterns.

The mathematical relationship module 138 can perform mathematical computations on various parameter values (such as invasive blood pressure, non-invasive blood pressure, respiration, temperature, carbon dioxide, oxygen saturation, heart rate, etc.) and/or combinations of parameter values to generate mathematical measurements that can be compared to acceptable numbers and/or ranges stored in or accessible by the decision support module 142 (as further discussed below). The mathematical relationship module 138 can also perform logistic regression analyses and compute outputs for various diagnostic equations used in the medical industry.

The decision support module 142 can include a table of ranges. The ranges can indicate various levels of the progression of heart disease for various medical parameters. The ranges can also correlate to any mathematical measurements generated by the mathematical relationship module 138, any ECG measurements generated by the pattern recognition module 134, and/or any image measurements generated by the pattern recognition module 134. In some embodiments, the decision support module 142 can provide a separate correlation based on the ECG measurements, the image measurements, or the mathematical measurements. In other embodiments, the decision support module 142 can provide a combined correlation based on any suitable combination of the ECG measurements, the image measurements, and the mathematical measurements. In one embodiment, the medical personnel reviewing the data can select the number of correlations displayed on the single medical report. For example, the medical personnel can select the correlation values for the ECG measurements, the image measurements, and the mathematical measurements to be separately displayed on the single medical report. In another example, the medical personnel can select to be displayed on the single medical report a correlation value for the correlation of the image measurements and the ECG measurements and a correlation value for the correlation of the mathematical measurements and the ECG measurements. The medical personnel can also select correlation values for additional combinations of ECG measurements, image measurements, and mathematical measurements to be displayed on the single medical report.

The software program 122 can also include a diagnosis module 158, which can operate to provide a medical diagnosis and/or a SCD risk score based on the ECG measurements, the image measurements, the mathematical measurements, and/or the correlations. The medical diagnosis can include an indication of any arrhythmia(s) or other cardiac conditions detected by the analysis module 130. The diagnosis module 158 can, in some embodiments, recommend medical treatments or follow-up tests. In some embodiments, the diagnosis module 158 can indicate that the data was inconclusive and/or that the SCD prediction system 110 cannot provide a diagnosis and/or a SCD risk score.

The SCD risk score can identify the level of susceptibility of the patient 10 to sudden cardiac death. The SCD risk score can also identify the parameters and the measurements that contributed to the SCD risk score. For example, the SCD prediction system 110 can provide a high SCD risk if the patient 10 has an ejection fraction less than about 30%, the patient 10 had a prior heart attack (as defined by wall motion abnormality or clinical condition), and the patient 10 is experiencing any one of the following: the QRS duration is greater than 120 ms, the signal-averaged ECG is greater than 140 ms, heart rate variability is abnormal, T-wave alternans are abnormal, or the heart rate turbulence is abnormal. Other determinations of sudden cardiac death using more or fewer parameters (including parameters not described herein) can be used and fall within the scope of the invention.

The software program 122 can also include a report module 162, which can provide to the medical personnel a single medical report that combines multiple independent tests based on multiple parameters. The single medical report can include one or more of the following: the SCD risk score, the measurements that contributed to the SCD risk score, the ECG measurements, the image measurements, the mathematical measurements, the normal and/or abnormal ranges for each parameter used to calculate the SCD risk score, medical diagnosis (with recommended treatment, as appropriate), graphs, charts, trends, ECGs, images with ECG indices, images identifying locations of problems, ECG data, ECG patterns, ECG correlations, image data, image patterns, image correlations, recommended follow-up tests, a patient identifier, patient history, a physician identifier, etc. The report module 162 can generate a single medical report to be displayed on a computer terminal screen or to be printed at a printer.

Figure 4:
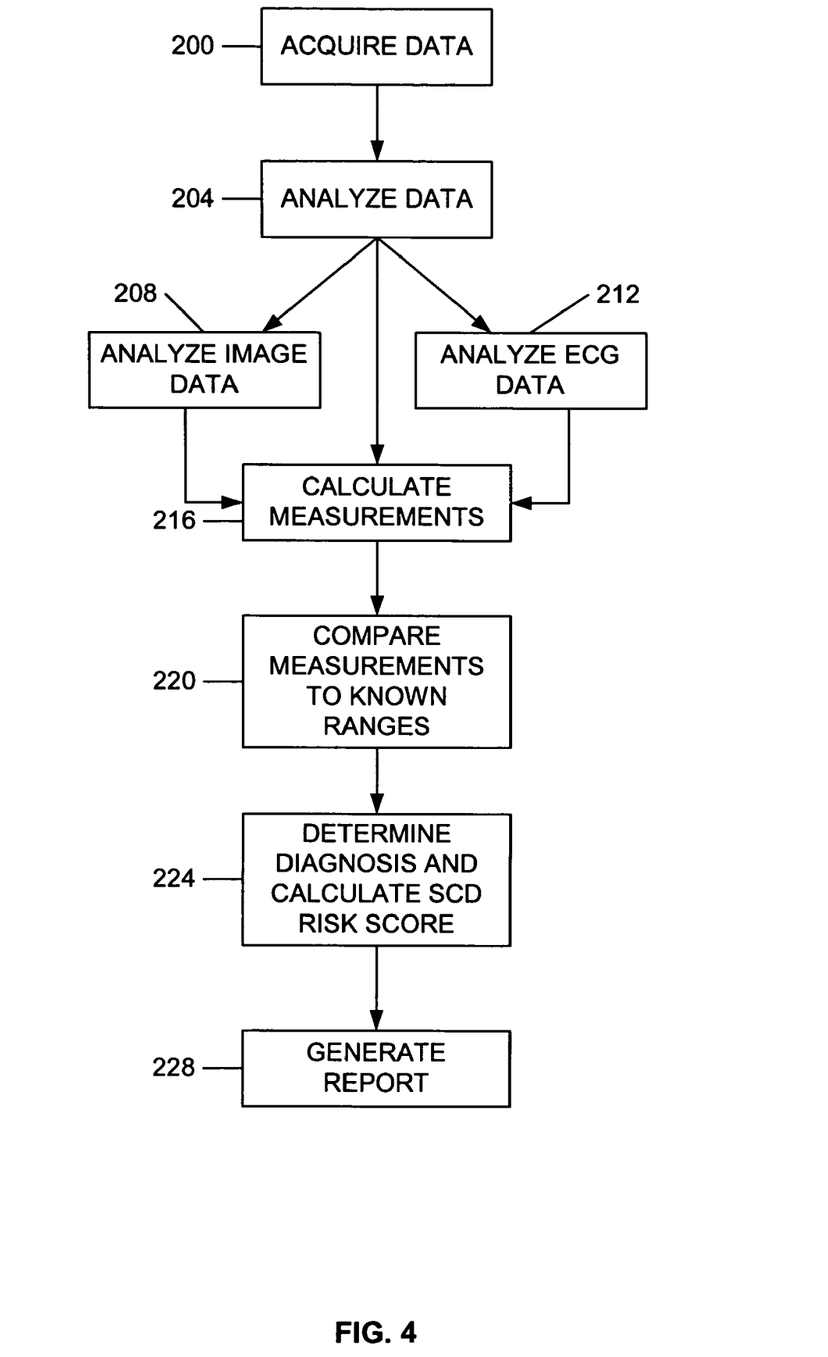
FIG. 4 is a flow chart illustrating the operation of the sudden cardiac death prediction system of FIG. 2 according to one embodiment of the method of the invention.

FIG. 4 is a flow chart illustrating one embodiment of the method of the invention. The SCD prediction system 110 can activate the software program 122 to acquire (at 200) data for the patient 10 using the acquisition module 126. The acquisition module 126 can communicate with and acquire the data from the databases 34, 46, 58, 70, 82, 94, and 118 via the network 22. The analysis module 130 can receive and analyze (at 204) the data. Any image data can be transmitted to the pattern recognition module 134 for analysis (at 208) with respect to stored image pattern(s) having known conditions and diagnoses. The analysis module 130 can detect and save the image measurements, including noted differences and similarities between the patient's images and the stored image pattern(s). Any ECG data can be transmitted to the pattern recognition module 134 for analysis (at 212) with respect to stored ECG pattern(s) having known conditions and diagnoses. The analysis module 130 can detect and save the ECG measurements, including noted similarities and differences between the patient's ECGs and the stored ECG pattern(s). The parameter values obtained during the various tests can be transmitted to the mathematical relationship module 138. The mathematical relationship module 138 can calculate (at 216) mathematical measurements based on any one parameter value and/or a combination of parameter values. The ECG measurements and image measurements as determined by the pattern recognition module 134 can also be combined with the various parameter values.

The decision support module 142 can receive the mathematical measurements, the ECG measurements, and the image measurements. The decision support module 142 can correlate or compare (at 220) the mathematical measurements, the ECG measurements, and the image measurements to their respective tables of ranges. In this manner, the decision support module 142 can determine the level of heart disease in the patient 10.

The diagnosis module 158 can receive the mathematical measurements, the ECG measurements, the image measurements, and the correlation data from the decision support module 142. The diagnosis module 158 can determine (at 224) a diagnosis and can calculate a SCD risk score for the patient. The diagnosis, the SCD risk score, and any other suitable data can be transmitted to the report module 162 to generate (at 228) a single medical report that combines multiple independent indications of sudden cardiac death from multiple pieces of medical equipment. The single medical report can be displayed at a computer terminal and/or printed for review by medical personnel.

Figure 5:
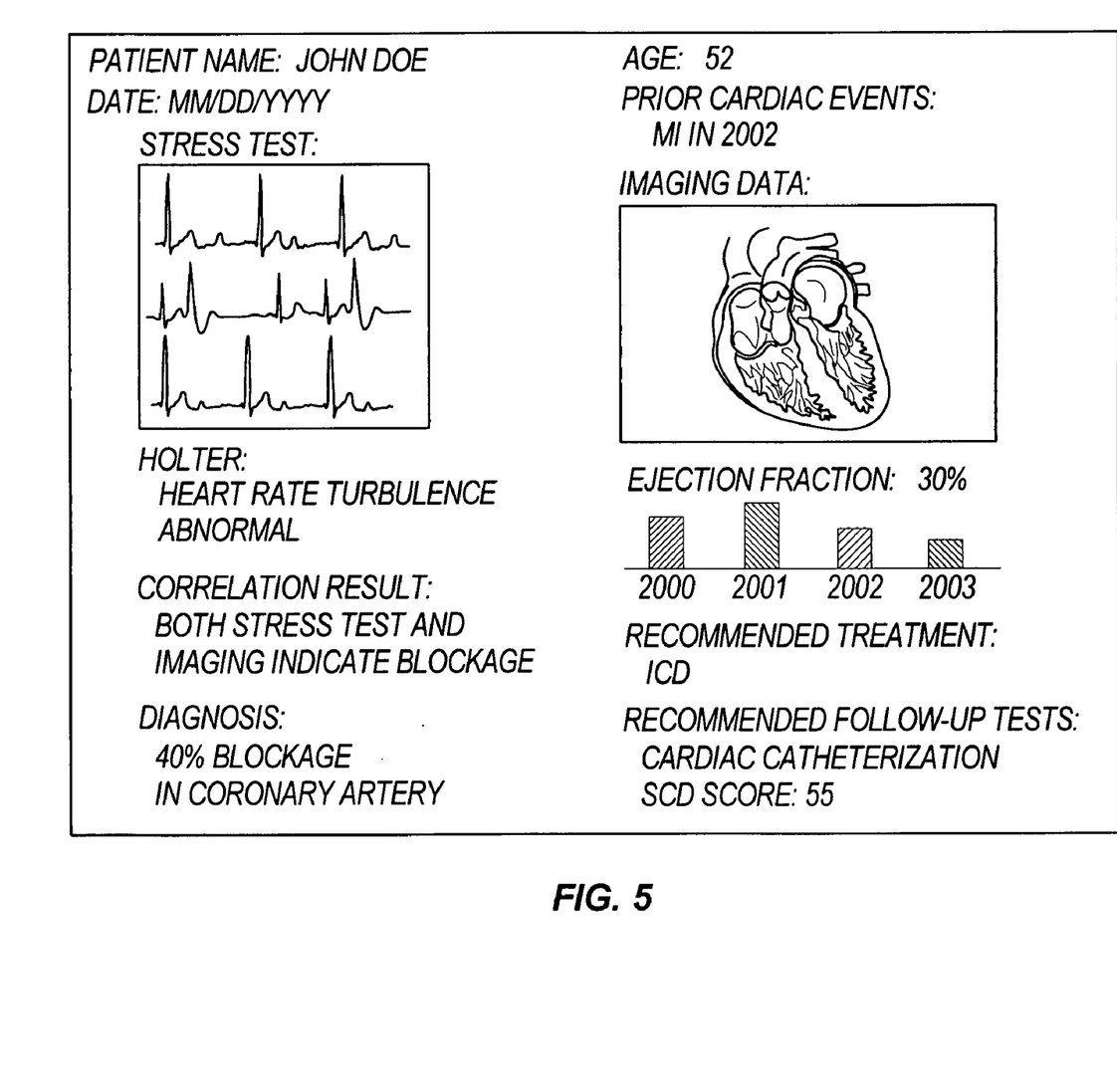
FIG. 5 illustrates a single medical report that can be generated by the sudden cardiac death prediction system of FIG. 2 according to one embodiment of the invention.

FIG. 5 illustrates an example of the single medical report generated by the report module 162. The single medical report can display one or more of the following: a patient identifier (e.g., name and age), patient history, the date the report was printed and/or the data was analyzed, ECG data from a stress test, image data, parameter values (e.g., ejection fraction), Holter test data results, correlation results with associated SCD risk score and diagnosis, recommended treatment, recommended follow-up tests, etc. The report module 162 can generate standard reports that include predetermined data and/or customized reports that can include data that is selected for display by the medical personnel.

Various features and advantages of the invention are set forth in the following claims.

What is claimed is:

1. A method of predicting sudden cardiac death in a patient, the method comprising:

acquiring patient data from a plurality of medical equipment databases with a set of acquisition devices;

comparing the patient data to stored patterns to determine a measurement with an analysis module;

comparing the measurement to a range to determine a correlation with a decision support module, wherein the correlation reflects a level of heart disease;

diagnosing a sudden cardiac death risk score with a diagnosis module; and generating a single report based on the patient data, wherein the single report includes the sudden cardiac death risk score and a set of electrocardiogram data, an electrocardiogram pattern, an electrocardiogram correlation, an electrocardiogram measurement, image data, an image pattern, an image correlation, an image measurement, a mathematical measurement, a parameter value, and a range.

2. The method of claim 1 and further comprising diagnosing the sudden cardiac death risk score based on at least one of an image correlation, an electrocardiogram correlation, and a mathematical correlation.

3. A computer program embodied by a computer readable medium capable of being executed by a computer, the computer program for use in a sudden cardiac death prediction system, the computer program comprising:

an acquisition module that communicates over a network to acquire patient data from plurality of medical equipment databases;

an analysis module that analyzes the patient data and calculates a plurality of measurements;

a decision support module that analyzes the plurality of measurements and determines a level of heart disease;

a diagnosis module that provides a medical diagnosis and sudden cardiac death prediction score based on the level of heart disease; and a report module that provides a single report including at least the sudden cardiac death prediction score, and further wherein the single report includes a set of electrocardiogram data, an electrocardiogram pattern, an electrocardiogram correlation, an electrocardiogram measurement, image data, an image pattern, an image correlation, an image measurement, a mathematical measurement, a parameter value, and a range.

4. The computer program of claim 3 wherein the single report further includes at least one of a diagnosis, a recommended treatment, a recommended follow-up test, a patient identifier, a patient history, and a physician identifier.

5. The computer program of claim 3, wherein the analysis module includes a pattern recognition module, the pattern recognition module accessing at least one of the electrocardiogram patterns and image patterns.

6. The computer program of claim 3 wherein the analysis module includes a mathematical relationship module.

7. A method of displaying a prediction of sudden cardiac death, the method comprising:

generating a single report based on data acquired from a plurality of medical devices,
the single report including a patient history and a physician identifier;
the single report including a set of electrocardiogram data, an electrocardiogram pattern, an electrocardiogram correlation, an electrocardiogram measurement, image data, an image pattern, an image correlation, an image measurement, a mathematical measurement, a parameter value, and a range; and
the single report including at least one of a sudden cardiac death risk score, a diagnosis, a recommended treatment, and a recommended follow-up test; and displaying the single report for review by medical personnel.

8. A sudden cardiac death prediction system comprising:

an acquisition module connected to a plurality of inputs for receiving patient data and image data from a plurality of databases;

means for analyzing the patient data and the image data to calculate a plurality of measurements;

a decision support module that analyzes the plurality of measurements and determines a level of heart disease; and a diagnosis module to generate a sudden cardiac death prediction score based on the level of heart disease; and a report module that provides a single report including at least the sudden cardiac death prediction score, and further wherein the single report includes a set of electrocardiogram data, an electrocardiogram pattern, an electrocardiogram correlation, an electrocardiogram measurement, image data, an image pattern, an image correlation, an image measurement, a mathematical measurement, a parameter value, and a range.

9. A medical device for determining a risk of sudden cardiac death, the medical device comprising:

an acquisition module operable to acquire ECG data and image data; and an analysis module operable to calculate a plurality of measurements based upon the ECG data and the image data;

a decision support module that analyzes the plurality of measurements and determines a level of heart disease; and a diagnosis module to generate a sudden cardiac death score based on the level of heart disease; and a report that provides a single report including at least the sudden cardiac death prediction score, and further wherein the single report includes a set of electrocardiogram data an electrocardiogram pattern, an electrocardiogram correlation, an electrocardiogram measurement, image data, an image pattern, an image correlation, an image measurement, a mathematical measurement, a parameter value, and a range.

* * * * *